US 11,521,715 B2

(12) United States Patent
Skaltsounis et al.

(10) Patent No.: US 11,521,715 B2
(45) Date of Patent: Dec. 6, 2022

(54) SYSTEM AND METHOD FOR PROMOTING, TRACKING, AND ASSESSING MENTAL WELLNESS (71) Applicants: Alexandria Brown Skaltsounis, West Hollywood, CA (US); Clenét Verdi-Rose, Los Angeles, CA (US)

(72) Inventors: Alexandria Brown Skaltsounis, West Hollywood, CA (US); Clenét Verdi-Rose, Los Angeles, CA (US)

(73) Assignees: Alexandria Brown Skaltsounis, West Hollywood, CA (US); Clenét Verdi-Rose, Los Angeles, CA (US)

( * ) Notice: Subject to any disclaimer, the term of this patent is extended or adjusted under 35 U.S.C. 154(b) by 0 days.

(21) Appl. No.: 17/183,673

(22) Filed: Feb. 24, 2021

(65) Prior Publication Data
US 2022/0270715 A1 Aug. 25, 2022

(51) Int. Cl.
| | |
|---|---|
| *G16H 10/20* | (2018.01) |
| *G16H 10/60* | (2018.01) |
| *G16H 50/70* | (2018.01) |
| *A61B 5/00* | (2006.01) |
| *G16H 15/00* | (2018.01) |
| *A61B 5/16* | (2006.01) |
| *G16H 20/70* | (2018.01) |

(52) U.S. Cl.
CPC ............ *G16H 10/20* (2018.01); *A61B 5/165* (2013.01); *A61B 5/4803* (2013.01); *G16H 10/60* (2018.01); *G16H 15/00* (2018.01); *G16H 20/70* (2018.01); *G16H 50/70* (2018.01)

(58) Field of Classification Search
CPC ....... A61M 2205/3592; A61N 1/36025; A61N 1/36082; G06F 16/2477; G16H 40/63; G16H 10/20; G16H 10/60; G16H 15/00; G16H 20/70; G16H 50/70; A61B 5/165; A61B 5/4803
See application file for complete search history.

(56) References Cited

U.S. PATENT DOCUMENTS

| | | | | |
|---|---|---|---|---|
| 5,437,634 | A | * 8/1995 | Amano | A61M 60/113 604/65 |
| 2002/0128866 | A1 | * 9/2002 | Goetzke | G16H 50/50 705/2 |
| 2005/0283385 | A1 | * 12/2005 | Hunkeler | G16H 50/30 705/2 |

(Continued)

*Primary Examiner* — Reginald R Reyes
(74) *Attorney, Agent, or Firm* — Maier & Maier, PLLC (57) ABSTRACT

A system and method for promoting, tracking, and assessing mental wellness. The method includes receiving an entry from a subject user, the entry including an input and a mood indicator, storing the entry in within a set of entries, the set including at least two entries received over a period of time, and determining a presence of at least one marker in the input of each entry within the set. The method further includes analyzing the set of entries for occurrences of markers or sequences of markers and alerting a supervisory user if the occurrences of markers or sequences of markers exceed a predetermined threshold. The method further includes associating contextual content from a supervisory user to an entry, the contextual content including a note, an attachment, a form, and/or a flag. The system includes a platform for accessing, managing, and storing data and analytics for implementing the method.

18 Claims, 5 Drawing Sheets

(56) References Cited

U.S. PATENT DOCUMENTS

| | | | | |
|---|---|---|---|---|
| 2006/0287883 A1* | 12/2006 | Turgiss | ................ | G06Q 10/10 702/19 |
| 2009/0264957 A1* | 10/2009 | Giftakis | ............ | A61N 1/36082 607/45 |
| 2015/0003595 A1* | 1/2015 | Yaghi | ................ | H04M 3/5175 379/85 |
| 2019/0008397 A1* | 1/2019 | Fine | .................... | A61B 5/0285 |

* cited by examiner

Fig. 4

SYSTEM AND METHOD FOR PROMOTING, TRACKING, AND ASSESSING MENTAL WELLNESS

BACKGROUND

While the focus on mental health has increased in recent decades, mental health resources utilizing technological advancements to provide insight into human development, emotion, and state of mind are frequently overlooked. Proactive and impartial mental health solutions are still lacking and it can be difficult to express and quantify how one may truly feel. For example, a child may be shy or not willing to express their actual feelings depending on the contextual circumstances. Furthermore, comprehensive solutions for tracking a subject user's mental health, moods, and feelings over extended terms of time, and for providing such information to supervisory users (e.g., clinicians) are also lacking. A solution that can provide a calm and nurturing place to practice positive mental health techniques and advance the collection of mental health data and analytics without bias and prejudice of analysis is therefore needed. A solution that can provide parents, caretakers, and professionals with detailed insight and analysis of the mental health of a subject user while providing contextual content management and streamlining traditional processes is therefore needed.

SUMMARY

According to at least one exemplary embodiment, a system, method, and computer program product for promoting, tracking, and assessing wellness are disclosed. The embodiments disclosed herein can be adapted to receive an entry, for example a journal and/or session entry, the entry including an input and a mood indicator, store the entry within a set of entries, the set of entries including at least two entries received over a period of time, and determine a presence of at least one marker or sequence of markers in the input of each entry within the set of entries. The embodiments disclosed herein can further be adapted to analyze the set of entries for occurrences of markers or sequences of markers and alert a supervisory user if the occurrences of markers or sequences of markers exceed a predetermined threshold.

The input can include a drawing, a text input, a video input, and an audio input. The contents of the video and audio input can be transcribed. The markers can include alert words, mood indicators, and percentages of color in a drawing, among other factors. The predetermined threshold can be a predetermined number of occurrences of the marker or sequence of markers within a predetermined amount of time or a predetermined percentage of occurrences of the marker or sequence of markers within the set of entries. The occurrence of markers or sequences of markers may further be correlated with occurrences of mood indicators. The embodiments disclosed herein can further be adapted to receive contextual content from a supervisory user and associate the contextual content to the entry. The contextual content may be one or more of a note, an attachment, a flag, a session recording, forms managed by the system, and other information. Such forms may include diagnostic, insurance, legal, and other forms. The comprehensive contextual system can be adapted to store mental-health-related data or any other relevant data for a user and can facilitate streamlining access to the data for a supervisory user.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Aspects of the invention are disclosed in the following description and related drawings directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein may be described in terms of sequences of actions to be performed by, for example, elements of a computing device. It should be recognized by those skilled in the art that the various sequence of actions described herein can be performed by specific circuits (e.g., application specific integrated circuits (ASICs)) and/or by program instructions executed by at least one processor. Additionally, the sequence of actions described herein can be embodied entirely within any form of computer-readable storage medium such that execution of the sequence of actions enables the processor to perform the functionality described herein. Thus, the various aspects of the present invention may be embodied in a number of different forms, all of which have been contemplated to be within the scope of the claimed subject matter. In addition, for each of the embodiments described herein, the corresponding form of any such embodiments may be described herein as, for example, "a computer configured to" perform the described action.

Figure 1:
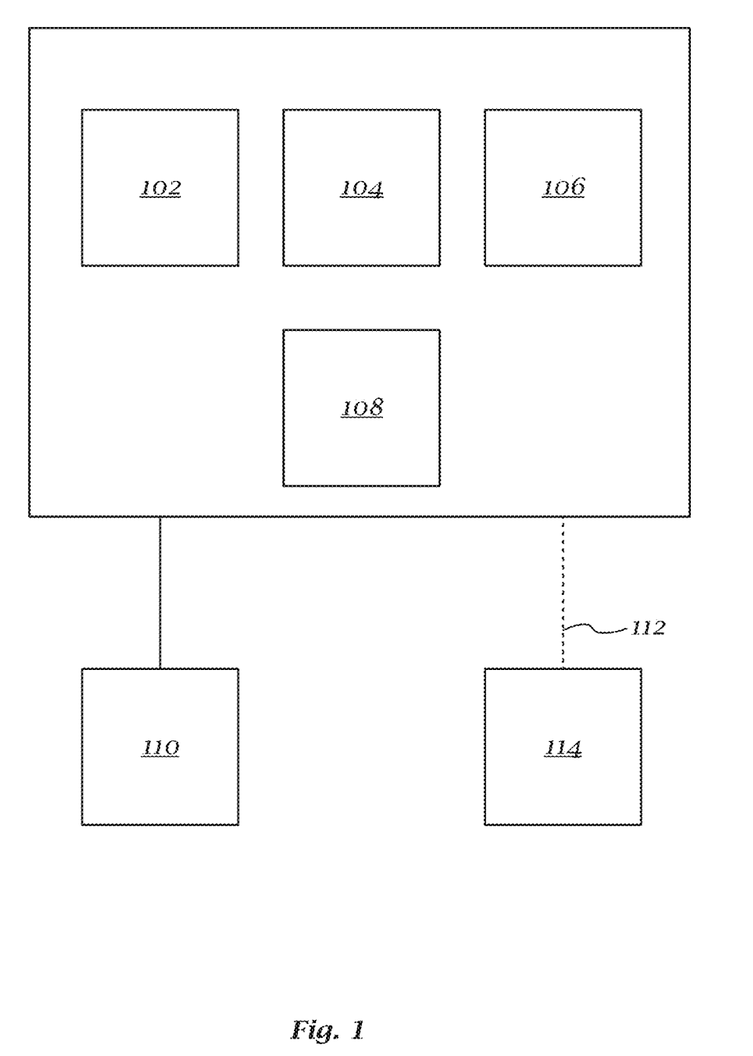
FIG. 1 shows an exemplary system for promoting, tracking, and assessing mental health and wellness.

According to at least one exemplary embodiment, a diagnostic system and method for promoting, tracking, and assessing mental health and wellness 100 is disclosed. As shown in FIG. 1, system 100 may include a plurality of modules that may be interacted with by a subject user or a supervisory user such as a parent, caretaker, or medical professional. For example, system 100 may include an entry module 102, an exercise module 104, and an analytics module 106. System 100 may further include one or more data storages 108, which may be any data storage and management implementation known in the art. In some exemplary embodiments, system 100 may be provided on a user-side computing device 110, such as, for example, as an application for a computer or a mobile device. In such embodiment, the various modules of system 100 and the data storage 108 may be present on the user-side computing device 110 and executed on device 110. In other exemplary embodiments, all or portions of system 100 may be provided on a cloud or communication network 112, which may be a wired or wireless network implemented via any communication technique known in the art. For example, data store 108 and analytics module 106 may be provided on a server side 114, while entry module 102 and exercise module 104 may be provided on the user-side computing device 110. In yet other exemplary embodiments, all components may be provided on the server side 114, and system 100 may be accessible via interfaces provided on user-side computing devices 110, such as, for example, a web-based application or a standalone application.

In some exemplary embodiments, entry module 102 and exercise module 104 may be oriented towards interaction with young children, for example, children who have not yet learned to write, or children in the 2-8-year-old range. For example, entry module 102 may include interfaces to allow a child to draw or speak to record their moods and feelings. In further exemplary embodiments, entry module 102 may also include interfaces for recording clinical sessions, for example between the subject user and a mental health counselor or other clinical professional. Exercise module 104 may include interactive, guided exercises to teach mental health and wellness principles. The various exercises of the exercise may include animated characters that speak and move to provide guidance for the child as to how to perform the exercises. For example, the exercises may include breathing exercises, mood exercises, guided relaxation and meditation, body exercises, empathy lessons showing how feelings manifest in the body, emotion identification lessons for autistic children, exercises for cultivating imagination, healthy nutrition and wellness habit lessons, and sound programs for aiding sleep. Analytics module 106 may provide interfaces and data analysis for parents, caretakers, health professionals, and the like. Analytics module 106 may utilize data obtained at least from entry module 102 to track a child's moods and mental health over time. In yet further exemplary embodiments, the modules of system 100 may be oriented towards interactions with subject users of different ages or needs. For example, the modules of system 100 may be oriented towards pre-teen users (i.e., ages 9-13), teenage users, adults experiencing PTSD, dementia, or other disabilities or illnesses. System 100 may further be utilized to aid in various settings, for example individual or group counseling sessions for various issues (for example, anger management, substance dependence, mental illness, and so forth). Additionally, system 100 may be further utilized in conjunction with algorithms, for example artificial intelligence algorithms, to provide further insight, track, or corroborate emotional verification or dissonance for a statement, opinion, or testimony.

Figure 2A:
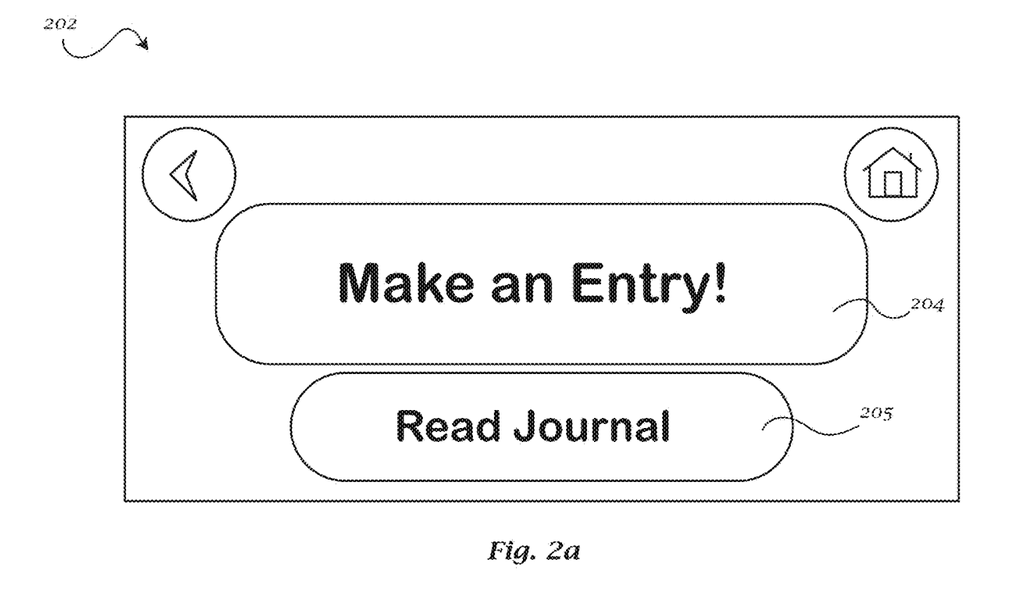
FIGS. 2a-2d show exemplary interfaces of the computer program product for promoting, tracking, and assessing mental health and wellness.
Figure 2B:
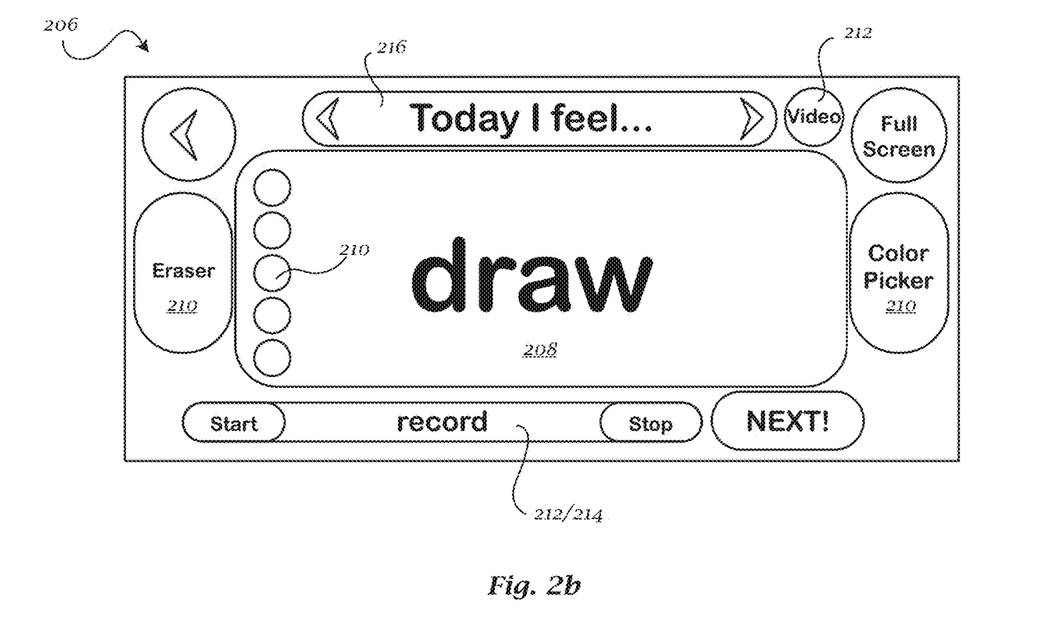

Turning to FIG. 2a, the entry module may include a plurality of interfaces for interaction with subject users. In such embodiments, the entries may include journal entries. The entry module can be adapted to receive drawn, written, spoken, and/or video input from the user. Interfaces of the entry module may be adapted to provide easy navigation and prompting to allow ease of interaction for subject users of system 100. In an exemplary embodiment, which may be adapted towards direct interaction with subject users, a first interface 202 may include options for making a journal entry 204 or reading journal entries 205. If the subject user selects to make a journal entry, an input interface 206 may be provided, as shown in FIG. 2b. The input interface 206 may include input tools such as a canvas 208, drawing and text tools 210, video record 212, and audio record 214. Furthermore, input interface 206 may include a journal prompt 216. Journal prompt 216 may present the subject user with a prompt for the journal entry. A default prompt may be initially presented and the subject user may select from a variety of additional prompts as well. For example, such prompts may include "Today I feel . . . ", "I am grateful for . . . ", "I got upset because . . . ", "I like myself because . . . ", "My dream is to . . . ", "I showed kindness when . . . ", and so forth. Journal entry prompts may be preloaded in the entry module, and custom prompts may also be created by a supervisory user. The subject user may select a desired prompt and then create a journal entry with the available input tools, such as the canvas 208 with drawing and text tools 210, video record 212, and audio record 214. Once the subject user has completed the journal entry using one or more of the input tools, a subsequent interface may be displayed by way of operation of a control such as a next button or the like.

Figure 2C:
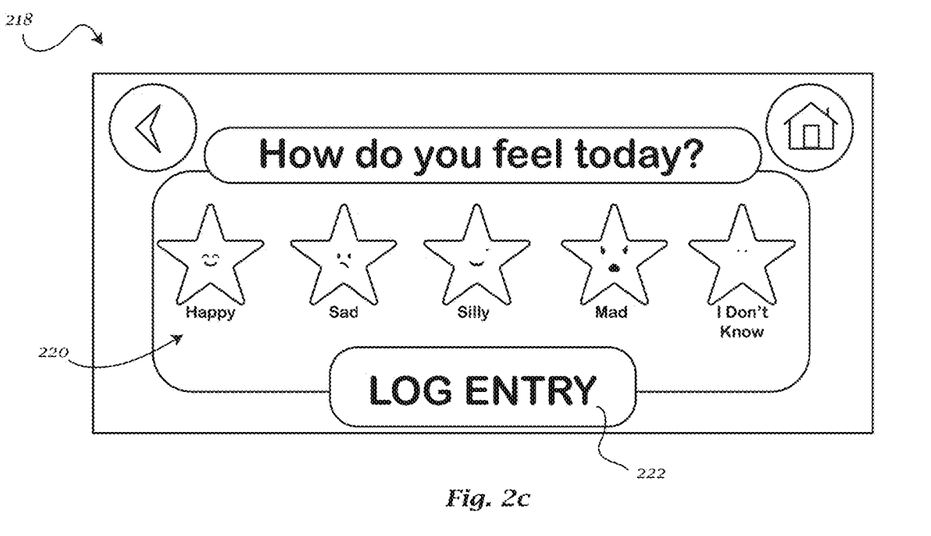

In some exemplary embodiments, the subsequent interface may be a mood interface 218, as shown in FIG. 2c. In the mood interface 218, the subject user may be prompted to choose a mood from a plurality of mood indicators 220, such as "happy", "sad", "silly", "mad", "I don't know", and so forth. Mood indicators may be preloaded in the entry module, and custom moods may also be created by a supervisory user. In some exemplary embodiments, the subject user may also be prompted to select a color from a spectrum of colors that the subject user feels matches their mood. After the subject user selects a mood indicator 220 and/or chooses a color, the subject user may log their entry by log entry control 222. The journal entries, including the drawn, text, and/or recorded inputs, along with the mood of the subject user may then be saved to data storage.

In yet further exemplary embodiments, entry module 102 may be adapted towards recording sessions between a subject user and a clinical professional, who may also be a supervisory user. In such embodiments, the entries of entry module 102 may include recordings of entire sessions, or portions of sessions, between the subject user and the clinical professional. The sessions may be logged, including the time, place, and duration of the session. Sessions may take place as remote sessions, with video and/or audio interaction being provided by system 100 on the computing devices or mobile devices of the subject user and the clinical professional. In addition, screen sharing functionality between the subject user and the clinical professional may be provided by system 100, such that both users can view a common interface on which interactions may be performed, including drawing, text input, mood selection, and so forth. Sessions may also take place as in-person sessions, with system 100 providing audio and/or video recording functionality of the session. Furthermore, session recordings (drawn, written, audio or video), and/or transcripts may be submitted from sources external to system 100 and may be classified as subject-user-submitted, supervisory-user-submitted, or other sessions by system 100. Subsequent to the recording of a session, the subject user may then be provided with mood interfaces, as described above.

Figure 2D:
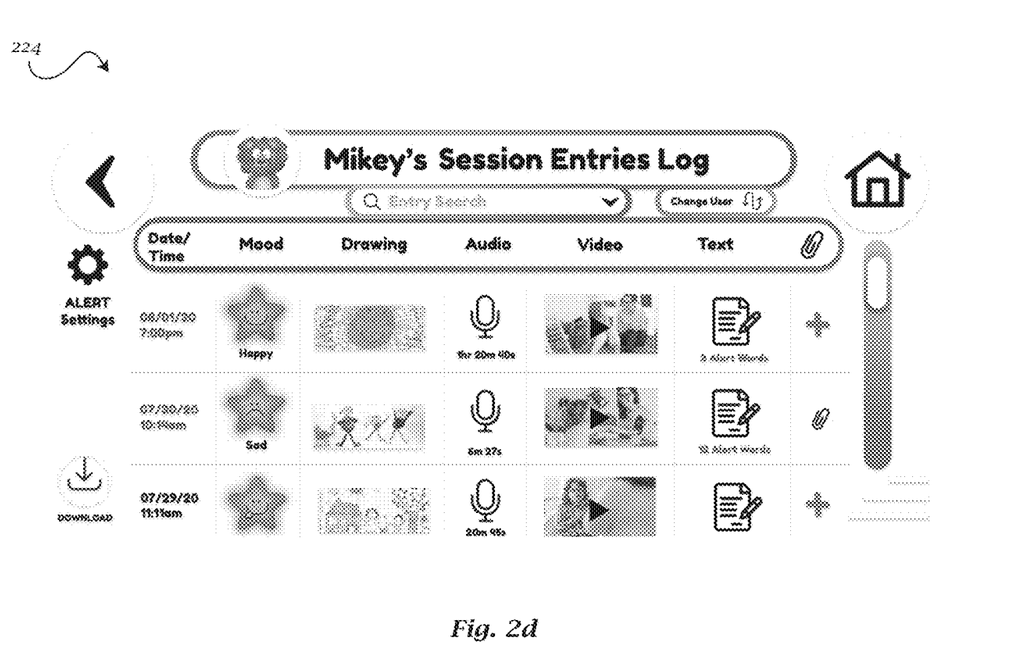

An entry log interface 224, for example as shown in FIG. 2d, may allow a user of system 100 to review past entries (i.e., journal and/or session entries), including the date and time the entry was logged, the mood, drawing, text, audio recording, and or video recording of the entry. A subject user or supervisory user may select any of the logged inputs for an entry to view the contents thereof. System 100 may also be provided with speech-to-text functionality adapted to transcribe contents of the audio and video recordings. The transcripts of the audio and video recordings may be provided with each entry.

In some exemplary embodiments, entry module 102 may provide additional features. For example, users such as supervisory users may be able to add notes, attachments, flags, and/or forms to any entry for future reference by the supervisory user. Notes may be available to be added to all inputs, i.e., logged drawings, text, videos, audio recordings, and transcriptions, and may be added to any temporal or spatial location in the input. Attachments may further be added to an entry, so as to provide comprehensive context for the entry. An attachment may be a document of any format, for example, text, image, video, PDF, and so forth. For example, if the subject user is a child, attachments may include items relevant to the particular entry of the subject user, such as report cards, social media posts, school projects or assignments, disciplinary items, and so forth. With respect to sessions, such attachments may include any forms from the clinical professional that are relevant to the session, any comments by the clinical professional on the session, and so forth. Such attachments may aid supervisory and subject users in creating a comprehensive log that may be reviewed subsequently or in a professional counseling context. Additionally, supervisory users may flag entries so as to provide further context for the entry. For example, a flag may be added to indicate that the entry was part of a high-stress incident in a subject user's life, a time-out, detention, episode, or so forth. Conversely, a flag may be added to indicate that the entry was part of a low-stress or pleasurable time in the subject user's life, such as a celebration, accomplishment, vacation, and so forth.

In some exemplary embodiments, supervisory users may be provided with interfaces directed towards features useful in a clinical environment. For example, such a clinical interface can facilitate maintaining audio and/or video recordings of sessions, which can then be associated to a user as entries for that user. The clinical entries can then be transcribed and analyzed by system 100 as described herein. The clinical interface can further provide for recording of both in-person and remote sessions. Additional features that may be provided by the clinical interface can include form creation and management, virtual waiting room, virtual chat with interactive features, video chat, fidget toggles, schedule management, diagnostic quizzes, and so forth.

A search feature may allow supervisory users to review the entries and associated notes and attachments and to determine trends. Searches may be performed by date and time, duration of recording, mood, entry content, amount of alert words per entry or sequences of alert words per entry, specific alert words or sequences of alert words, or the like. Alert settings may further be provided. For example, a supervisory user can define alerts based on a keyword, a mood, a frequency or repetition of a key word or mood throughout several entries, percentage of a color used in a drawing, and so forth. Alerts may be provided within the interfaces of the user-side applications of system 100, and may also be provided as push notifications on a supervisory user's mobile or personal device. The alert functionality may further be enhanced by analytics module 106.

Analytics module 106 may be adapted to analyze subject users' entries and provide comprehensive analysis and insights to supervisory users of the subject users' moods and mental health over time. For example, analytics module 106 may collect data regarding the date, length, frequency, and relative amount of usage of entry module 102, the usage and selected exercises of exercise module 104, and so forth. Analytics module 106 may further utilize speech-to-text functionality so as to transcribe the contents of the audio and video recordings of journal entries made by the subject user or by a supervisory user interacting with a subject user.

Analytics module 106 may further utilize artificial intelligence algorithms to analyze the transcribed text of entries and determine the existence of any desired key words or alert words in the entries. For example, alert words may include such terms as "sad", "angry", "mad", "upset", "cry", "bully", "nightmare", and so forth. Alert words may also include terms such as "happy", "joy", "fun", "friend", and so forth. A pre-defined set of alert words or sequences of alert words may be provided, and a supervisory user may add and remove alert words as desired to customize the alert functionality for a particular subject user. For example, a supervisory user may recognize that a subject user has a reaction to a certain person's name or a certain topic. Such alert words may then be added to the set of alert words or set of sequences of alert words.

Analytics module 106 may be adapted to notify a supervisory user based on an occurrence of markers. Markers may include concern markers and positive markers. For example, a concern marker may be a "negative" alert word or a lack of a "positive" alert word, while a positive marker may be a "positive" alert word or a lack of a "negative" alert word. As a further example, if a certain alert word or sequence of alert words occurs more than an indicated number of times within a particular timeframe, or with a higher than indicated frequency, analytics module 106 may alert the user. Conversely, if a certain alert word or sequence of alert words occurs less than an indicated number of times within a particular timeframe, or with a lower than indicated frequency, analytics module 106 may likewise alert the user. For example, a supervisory user may be alerted if a subject user used the word "mad" three times consecutively, or used the word "happy" less than twice a week. Furthermore, analytics module 106 may be adapted to notify a supervisory user based on an occurrence of concern markers such as a particular color in a subject user's drawing. For example, if a certain color is used in a large percentage of a drawing, and/or if such usage occurs more than an indicated number of times within a particular timeframe, or with a higher than indicated frequency, analytics module 106 may alert the supervisory user. For example, a supervisory user may be alerted if a subject user used the color red for 50% or more of a drawing in four or more entries.

Analytics module 106 may further track and correlate other aspects of a subject user's interaction with system 100. The subject user's moods logged in association with entries may be analyzed for frequency, repetition, and correlation with other aspects of the subject user's entries. Notes and attachments associated with entries may further be analyzed so as to determine correlations between moods, input content, and external influences on the subject user.

Analytics module 106 may utilize several methods and algorithms, for example AI or machine-learning algorithms, to perform the analysis of entries. For example, analytics module 106 may be adapted to detect colors, shapes, and subject matter of drawn entries, as well as alert words, common patterns of words, and sequences of words. In some exemplary embodiments, analytics module 106 may further be adapted to detect facial expressions, body language, and voice intonations in video and/or audio recorded entries, so as to provide further insight on the emotions of the subject user. In some exemplary embodiments, analytics module 106 may further be adapted to detect a subject user's cognitive dissonance or distortions throughout an entry. In yet further exemplary embodiments, analytics module 106 may be adapted to utilize artificial intelligence for predictive analytics. Analytics module 106 may further analyze anonymized data from a plurality of user accounts of system 100 so as to predict patterns of concern or positive mental health trajectories. Furthermore, system 100 may utilize artificial intelligence to detect early stage issues, protect subject users in dangerous situations or settings, and to predict common data trends with varying early-stage mental health diagnoses. Over time, such functionality may be adapted to analyze entries to detect early stages of abuse, data commonalities preceding a mental health diagnoses, and other predictive patterns related to mental health and wellness.

Figure 3:
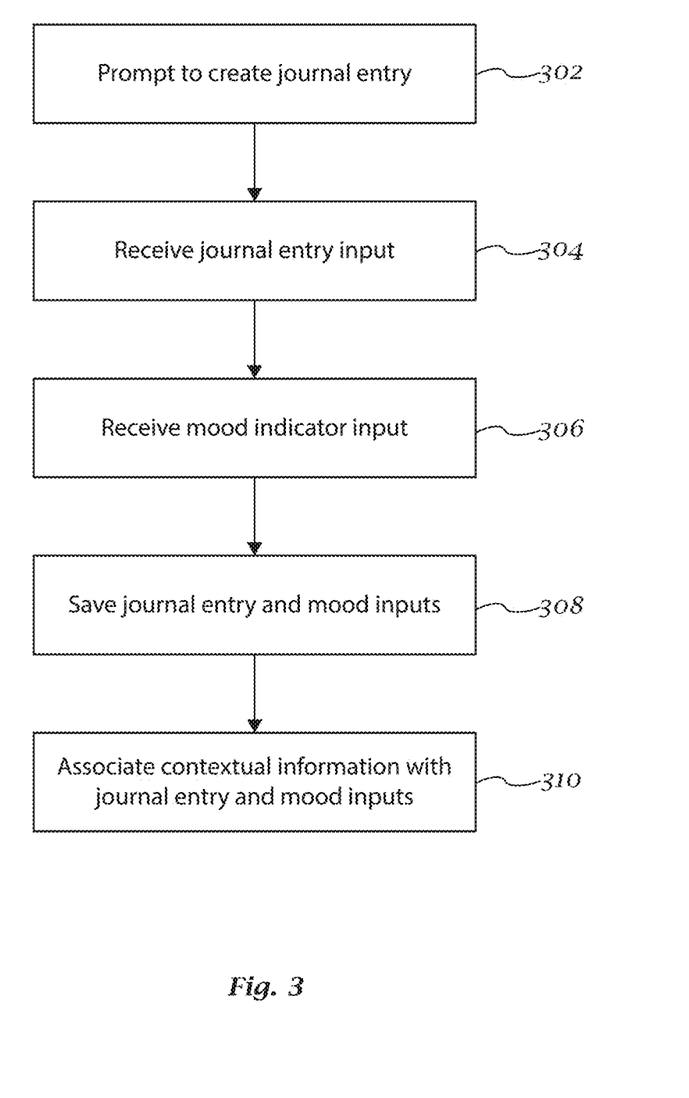
FIG. 3 shows an exemplary method for receiving mental wellness information.

FIG. 3 shows an exemplary method 300 for receiving mental wellness information. At step 302, a prompt to create an entry may be presented to a user, such as a subject user or a clinical professional. At step 304, input information for the entry may be received, including drawing input, text input, video input, and/or audio input. Input information may include journal entry information and/or session entry information. At step 306, a mood indicator may be received and associated with the input information for the entry. The mood indicator may include a description of the mood and/or a color associated with the mood. At step 308, the entry and associated mood indicators may be saved to data storage. In some embodiments, AI algorithms may further be used to analyze the entirety of the entry to determine mood. Optionally, at step 310, contextual information may be received from a supervisory user and associated with the entry in data storage. The contextual information may include notes, attachments, forms, and/or flags. At step 312, the recorded inputs, such as the drawing, audio, and video inputs, may be transcribed and associated with the entry in data storage.

Figure 4:
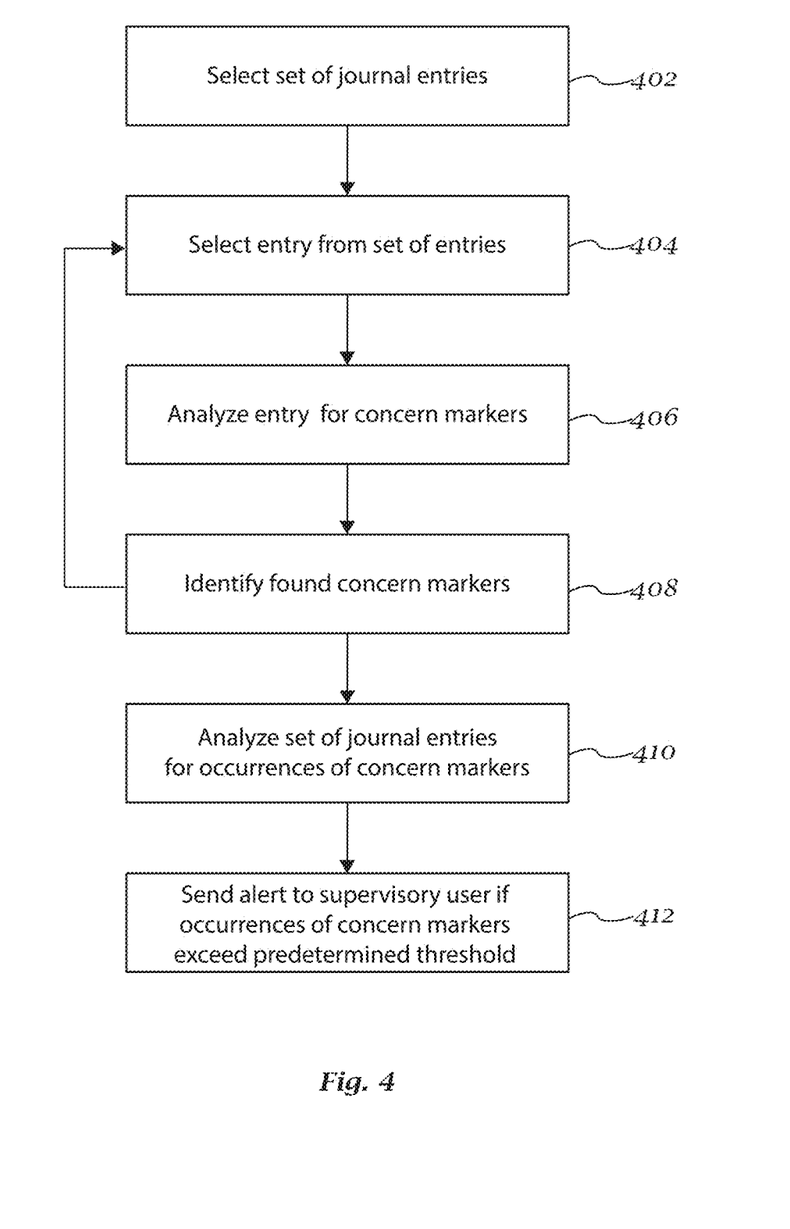
FIG. 4 shows an exemplary method for analyzing mental wellness information.

FIG. 4 shows an exemplary method 400 for analyzing mental wellness information. At step 402, a set of entries may be selected in data storage. At step 404, an entry from the set of entries may be selected. At step 406, the selected entry may be analyzed, for example by an AI algorithm, for markers, including concern markers and positive markers. Such markers may include, for example, the presence of alert words and/or sequences of alert words in the transcription of a recorded input, the presence of certain colors in a drawing input, a certain mood indicator, a color associated with a certain mood, and so forth. When found, the markers may be identified within the entry, at step 408. For example, alert words may be highlighted in the transcription of the recorded input. Steps 404-408 may be repeated for each entry in the set of entries.

At step 410, the plurality of entries may be analyzed for occurrences of markers or sequences of markers within the plurality of entries. The analysis may be based on several factors, such as frequency of occurrence of markers or sequences of markers within a predetermined time frame, absolute number of occurrences of markers or sequences of markers, a percentage of a marker or sequence of markers within an input, as well as correlations between occurrences of markers or sequences of markers and occurrences of other terms in the entries and correlations between occurrences of markers or sequences of markers and content of notes and attachments. If the occurrences of markers exceed a predetermined threshold, an alert or notification may be sent to a supervisory user, at step 412.

Logged usage data may further be used to provide trends and patterns regarding a subject user's interaction with system 100. The usage of the entry and exercise modules of system 100 may be logged, for every instance of use of the application. The logged data may then be displayed, for example as a graph that shows the amount of usage of the entry module and each exercise of the exercise module over time. The moods entered by the subject user at every instance of use of system 100, and/or those detected by AI algorithm analysis, may be logged and displayed as a graph showing the occurrence of each mood over time. Supervisory users may utilize such graphs to find trends and patterns that correlate with external stressors and points of concern, and to reinforce areas that improve the mental wellness of the subject user.

The embodiments disclosed herein can therefore provide a means of expression for a subject user, where the subject user may be comfortable in expressing themselves in ways that they may not feel comfortable expressing to a supervisory user and to learn healthy exercises and mindfulness techniques. The embodiments disclosed herein can further provide a means for parents, caretakers, and professionals to obtain insight into the day-to-day feelings of the subject user, to understand correlations between the subject user's moods and external stressors, and to obtain context for the subject user's moods and emotions, and obtain insight without bias and prejudice of analysis.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for promoting, tracking, and assessing mental wellness, comprising:
   providing a plurality of user-side interfaces on a plurality of user-side computing devices, each of the plurality of user-side interfaces communicatively coupled to a cloud server, wherein an individual user-side interface of the plurality of user-side interfaces for a subject user among a plurality of users allows the subject user to select a type of user-created input that is to be created by the subject user and to create the user-created input, the individual user-side interface comprising: selection elements for the subject user to select the type of user-created input, creation elements for creating the user-created input and corresponding to the type of user-created input, and mood entry elements for the subject user to input a mood indicator;
   receiving an entry from a subject user, the entry comprising the user-created input and the mood indicator;
   transmitting the received entry from the subject user to a remote database in communication with the cloud server;
   storing the entry within a set of entries on the remote database on a server-side non-transitory computer-readable medium, the set of entries comprising one or more entries received over a period of time and associated with the subject user;
   comparing anonymized data from the plurality of users to the one or more entries;

determining, by machine-learning with an analytics module stored on the server-side non-transitory computer-readable medium, a presence of at least one marker created by the subject user, the at least one marker being present in the content of the user-created input of each entry within the set of entries;

analyzing the set of entries for occurrences of the at least one marker or sequences of markers;

determining that the entry is a concern marker based on the comparison of the anonymized data from the plurality of users to the one or more entries received over the period of time and associated with the subject user; and transmitting an alert in real time, as at least one of a displayed notification and a push notification, from the analytics module to one or more user-side interfaces associated with one or more supervisory users, upon a determination by the analytics module that occurrences of concern markers exceed a predetermined threshold of concern markers in a predetermined timeframe set for the subject user among the plurality of users, wherein the user-created input is one or more of a drawing input created by the subject user, a text input created by the subject user, a video input created by the subject user, and an audio input created by the subject user.

2. The method of claim 1, further comprising:
transcribing content of the video input and/or the audio input.

3. The method of claim 1, wherein the at least one marker is an alert word created by the subject user.

4. The method of claim 1, wherein the at least one marker is the mood indicator inputted by the subject user.

5. The method of claim 1, wherein the at least one marker is a percentage of a color in a drawing that is greater than a predetermined amount, the drawing having been created by the subject user.

6. The method of claim 1, further comprising:
receiving contextual content from a supervisory user; and
associating the contextual content to the entry, wherein the contextual content comprises one or more of a note, an attachment, a form, and a flag.

7. The method of claim 1, wherein the predetermined threshold is a predetermined number of occurrences of the at least one marker or the sequence of markers within a predetermined amount of time.

8. The method of claim 1, wherein the predetermined threshold is a predetermined percentage of occurrences of the at least one marker or the sequence of markers within the set of entries.

9. The method of claim 1, further comprising:
correlating occurrences of the at least one marker or the sequences of markers with occurrences of mood indicators.

10. A computer program product, comprising:
a non-transitory computer-usable medium having a computer-readable program code embodied therein for promoting, tracking, and assessing mental wellness, said computer readable program code adapted to execute the steps of:
providing a plurality of user-side interfaces on a plurality of user-side computing devices, each of the plurality of user-side interfaces communicatively coupled to a cloud server, wherein an individual user-side interface of the plurality of user-side interfaces for a subject user among a plurality of users allows the subject user to select a type of user-created input that is to be created by the subject user and to create the user-created input, the individual user-side interface comprising: selection elements for the subject user to select the type of user-created input, creation elements for creating the user-created input and corresponding to the type of user-created input, and mood entry elements for the subject user to input a mood indicator;

receiving an entry from the subject user, the entry comprising the user-created input and the mood indicator;

transmitting the received entry from the subject user to a remote database in communication with the cloud server;

storing the entry within a set of entries on the remote database on a server-side non-transitory computer-readable medium, the set of entries comprising one or more entries received over a period of time and associated with the subject user;

comparing anonymized data from the plurality of users to the one or more entries;

determining, by machine-learning with an analytics module stored on the server-side non-transitory computer-readable medium, a presence of at least one marker created by the subject user, the at least one marker being present in the content of the user-created input of each entry within the set of entries;

analyzing the set of entries for occurrences of the at least one marker or sequences of markers;

determining that the entry is a concern marker based on the comparison of the anonymized data from the plurality of users to the one or more entries received over the period of time and associated with the subject user; and transmitting an alert in real time, as at least one of a displayed notification and a push notification, from the analytics module to one or more user-side interfaces associated with one or more supervisory users, upon a determination by the analytics module that occurrences of concern markers exceed a predetermined threshold of concern markers in a predetermined timeframe set for the subject user among the plurality of users, wherein the user-created input is one or more of a drawing input created by the subject user, a text input created by the subject user, a video input created by the subject user, and an audio input created by the subject user.

11. The computer program product of claim 10, further comprising:
transcribing content of the video input and/or the audio input.

12. The computer program product of claim 10, wherein the at least one marker is an alert word created by the subject user.

13. The computer program product of claim 10, wherein the at least one marker is the mood indicator inputted by the subject user.

14. The computer program product of claim 10, wherein the at least one marker is a percentage of a color in a drawing that is greater than a predetermined amount, the drawing having been created by the subject user.

15. The computer program product of claim 10, further comprising:
receiving contextual content from a supervisory user; and
associating the contextual content to the entry, wherein the contextual content comprises one or more of a note, an attachment, a form, and a flag.

16. The computer program product of claim 10, wherein the predetermined threshold is a predetermined number of occurrences of the at least one marker or the sequence of markers within a predetermined amount of time.

17. The computer program product of claim 10, wherein the predetermined threshold is a predetermined percentage of occurrences of the at least one marker or the sequence of markers within the set of entries.

18. The computer program product of claim 10, further comprising:
- correlating occurrences of the at least one markers or the sequences of markers with occurrences of mood indicators.

\* \* \* \* \*